(12) United States Patent
Baril et al.

(10) Patent No.: US 11,246,601 B2
(45) Date of Patent: Feb. 15, 2022

(54) ELONGATED ASSEMBLIES FOR SURGICAL CLIP APPLIERS AND SURGICAL CLIP APPLIERS INCORPORATING THE SAME

(71) Applicant: Covidien LP, Mansfield, MA (US)

(72) Inventors: Jacob C. Baril, Norwalk, CT (US); Roy J. Pilletere, North Haven, CT (US); Justin Thomas, New Haven, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 342 days.

(21) Appl. No.: 16/432,972

(22) Filed: Jun. 6, 2019

(65) Prior Publication Data

US 2020/0046366 A1 Feb. 13, 2020

Related U.S. Application Data

(60) Provisional application No. 62/717,952, filed on Aug. 13, 2018.

(51) Int. Cl.
*A61B 17/12* (2006.01)
*A61B 17/128* (2006.01)
(Continued)

(52) U.S. Cl.
CPC ...... *A61B 17/1285* (2013.01); *A61B 17/1227* (2013.01); *A61B 17/2909* (2013.01);
(Continued)

(58) Field of Classification Search
CPC ............ A61B 17/1285; A61B 17/1227; A61B 17/2909; A61B 17/122; A61B 17/128;
(Continued)

(56) References Cited

U.S. PATENT DOCUMENTS

| 3,120,230 A | 2/1964 | Skold |
| 3,363,628 A | 1/1968 | Wood |

(Continued)

FOREIGN PATENT DOCUMENTS

| AU | 2013254887 A1 | 11/2013 |
| CA | 1163889 A | 3/1984 |

(Continued)

OTHER PUBLICATIONS

Extended European Search Report issued in Appl. No. EP 19191225.2 dated Feb. 6, 2020 (10 pages).

(Continued)

*Primary Examiner* — Erich G Herbermann

(57) ABSTRACT

A surgical clip applier and an elongated assembly thereof. The elongated assembly includes an outer shaft, an end effector assembly extending distally from the outer shaft and including first and second spaced-apart arms having first and second jaws disposed at respective free ends thereof, and an inner drive sleeve including a bearing assembly slidably disposed about the end effector assembly. The bearing assembly includes first and second bearing rollers positioned adjacent the first and second spaced-apart arms. Sliding of the bearing assembly from a proximal position to a distal position rolls the bearing rollers along the spaced-apart arms to urge the first and second spaced-apart arms towards one another, thereby moving the first and second jaws from a spaced-apart position to an approximated position to apply a surgical clip about tissue disposed between the first and second jaws.

20 Claims, 8 Drawing Sheets

US 11,246,601 B2

Page 2

(51) Int. Cl.
*A61B 17/122* (2006.01)
*A61B 17/29* (2006.01)
*A61B 17/00* (2006.01)

(52) U.S. Cl.
CPC ............... A61B 2017/0046 (2013.01); *A61B 2017/00367* (2013.01)

(58) Field of Classification Search
CPC .......... A61B 17/29; A61B 2017/00367; A61B 2017/0046; A61B 2017/00473; A61B 2017/00845; A61B 2017/2902; A61B 2017/2939; A61B 2017/2946
See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |

(56) References Cited

U.S. PATENT DOCUMENTS

| | | |
|---|---|---|
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,032,849 A | 3/2000 | Mastri et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |

(56) References Cited

U.S. PATENT DOCUMENTS

| | | |
|---|---|---|
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |

(56) References Cited

U.S. PATENT DOCUMENTS

| | | |
|---|---|---|
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |

(56) References Cited

U.S. PATENT DOCUMENTS

| | | |
|---|---|---|
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,440 B2 | 10/2016 | Schulz et al. |
| 9,468,444 B2 | 10/2016 | Menn et al. |
| 9,469,440 B1* | 10/2016 | Flood ................ A45C 3/001 |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0082952 A1* | 4/2004 | Dycus ............... A61B 18/1445<br>606/51 |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0006429 A1 | 1/2005 | Wales et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |

(56) References Cited

U.S. PATENT DOCUMENTS

| | | |
|---|---|---|
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0188872 A1* | 8/2008 | Duff .................... A61B 17/122 606/142 |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Veh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0085516 A1* | 4/2013 | Kerr .................. A61B 18/1442 606/167 |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0151073 A1 | 6/2016 | Castro et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049446 A1 | 2/2017 | Scholten et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 004605911 B | 2/2017 |
| DE | 20 2005 001664 U1 | 5/2005 |
| DE | 202007003398 U1 | 6/2007 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 1908414 A2 | 4/2008 |
| EP | 2524660 A1 | 11/2012 |
| EP | 2606835 A2 | 6/2013 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017075752 A1 | 5/2017 |

OTHER PUBLICATIONS

Extended European Search Report issued in Appl. No.: EP 19191229.4 dated Jan. 16, 2020 (5 pages).

* cited by examiner

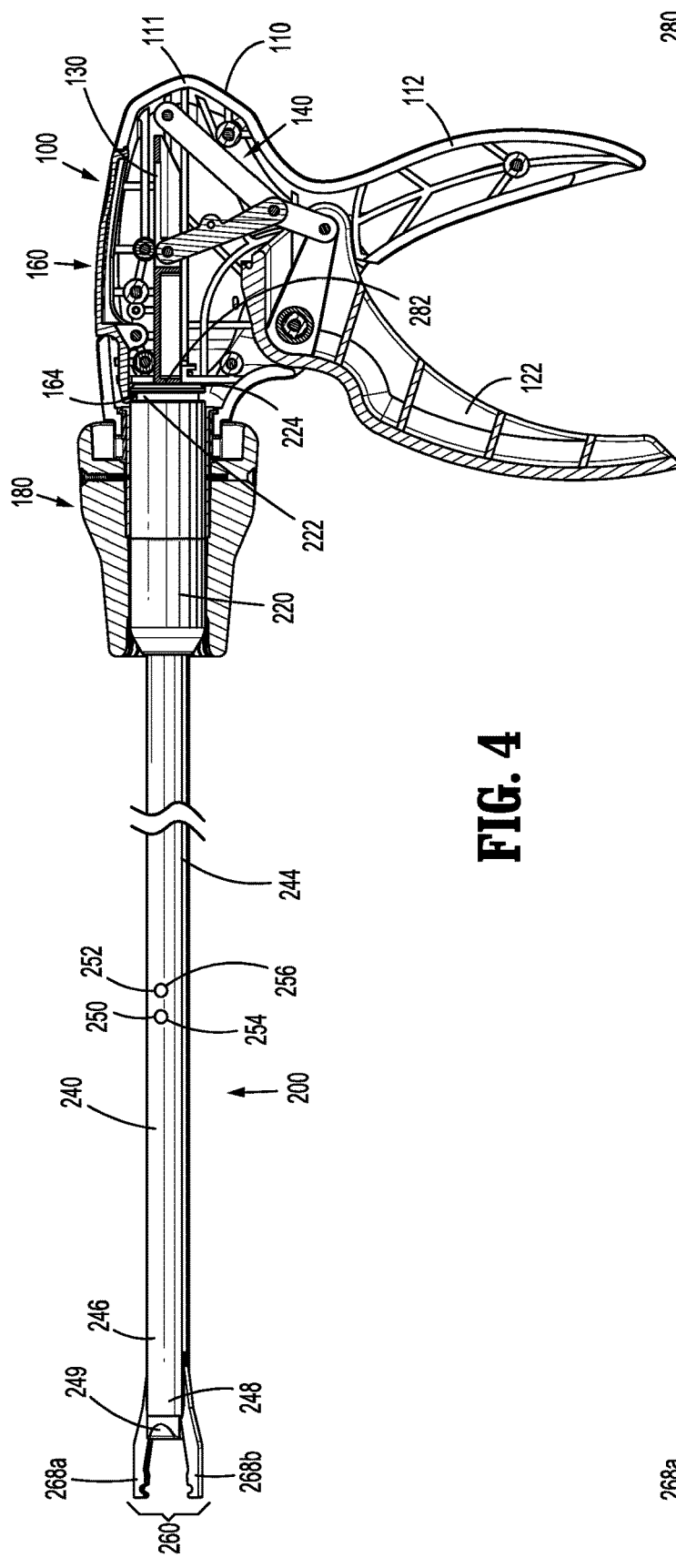
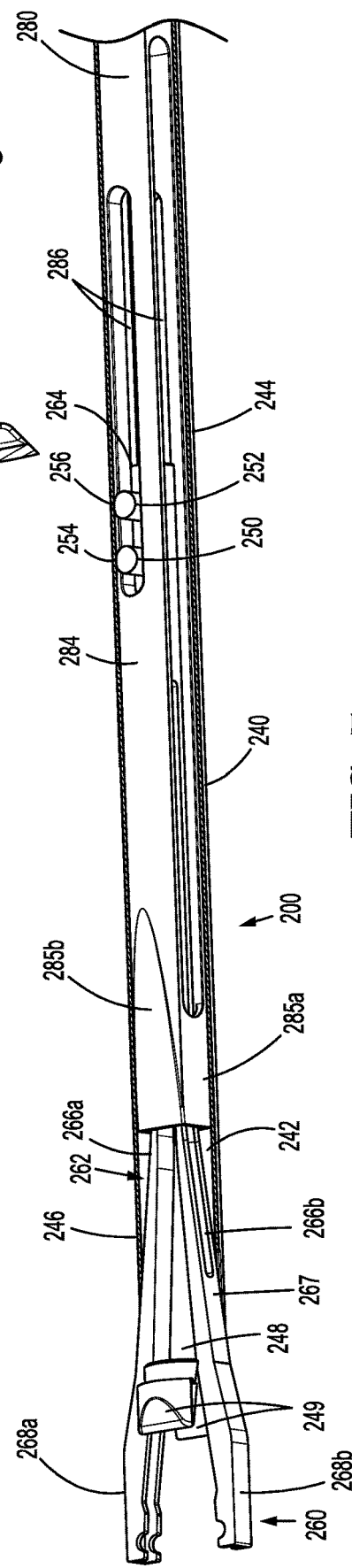
FIG. 4
FIG. 5

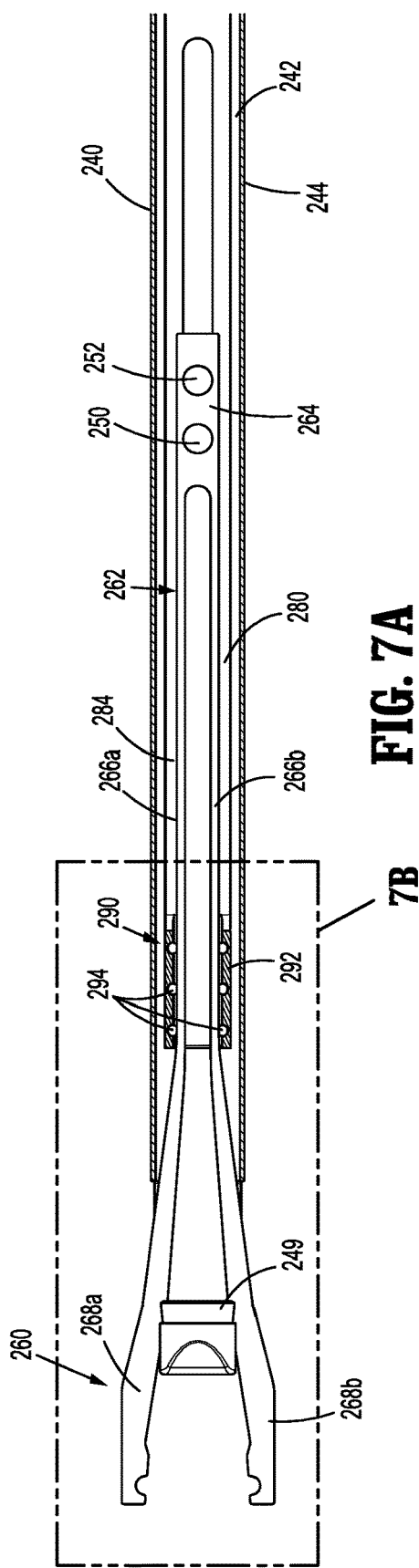
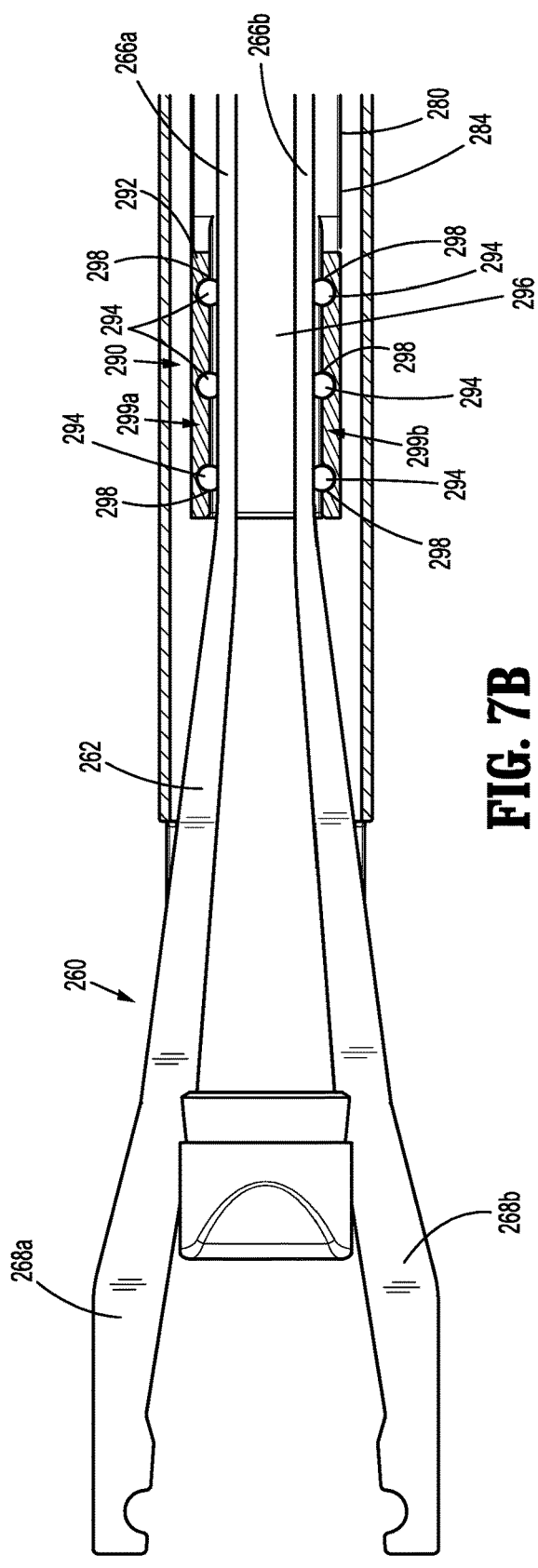
FIG. 7A
FIG. 7B

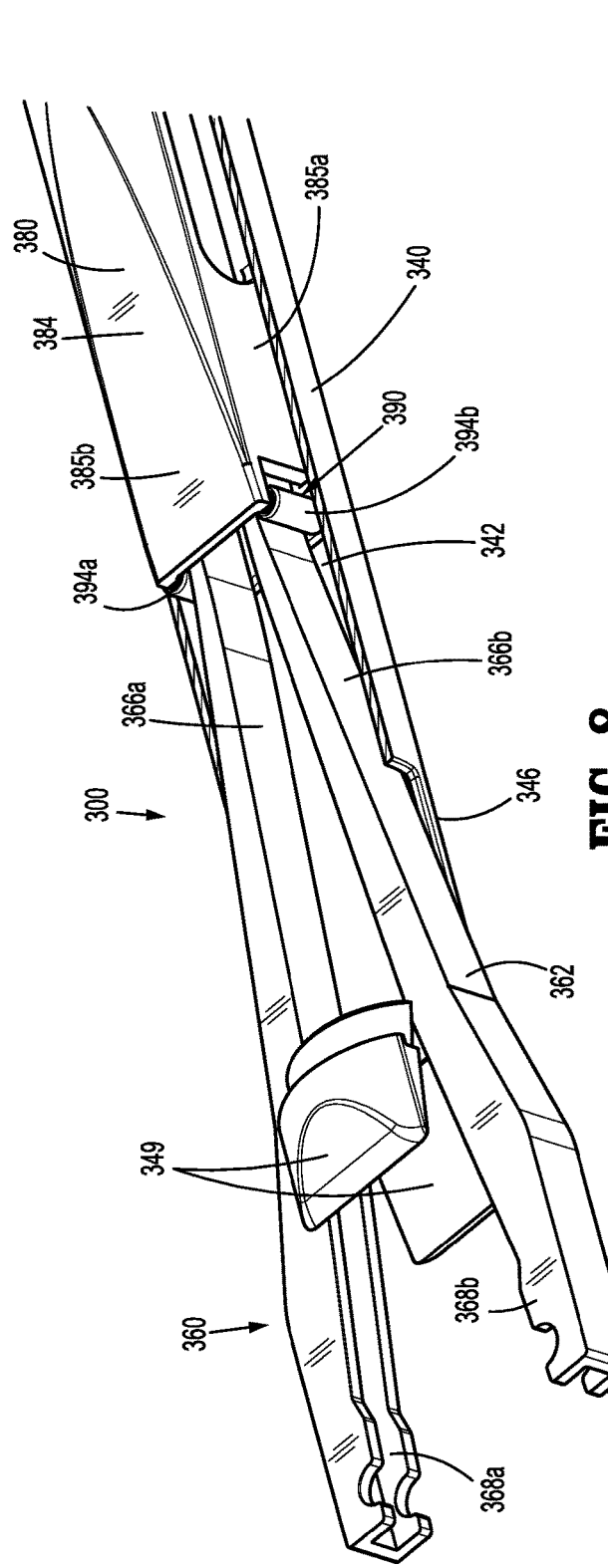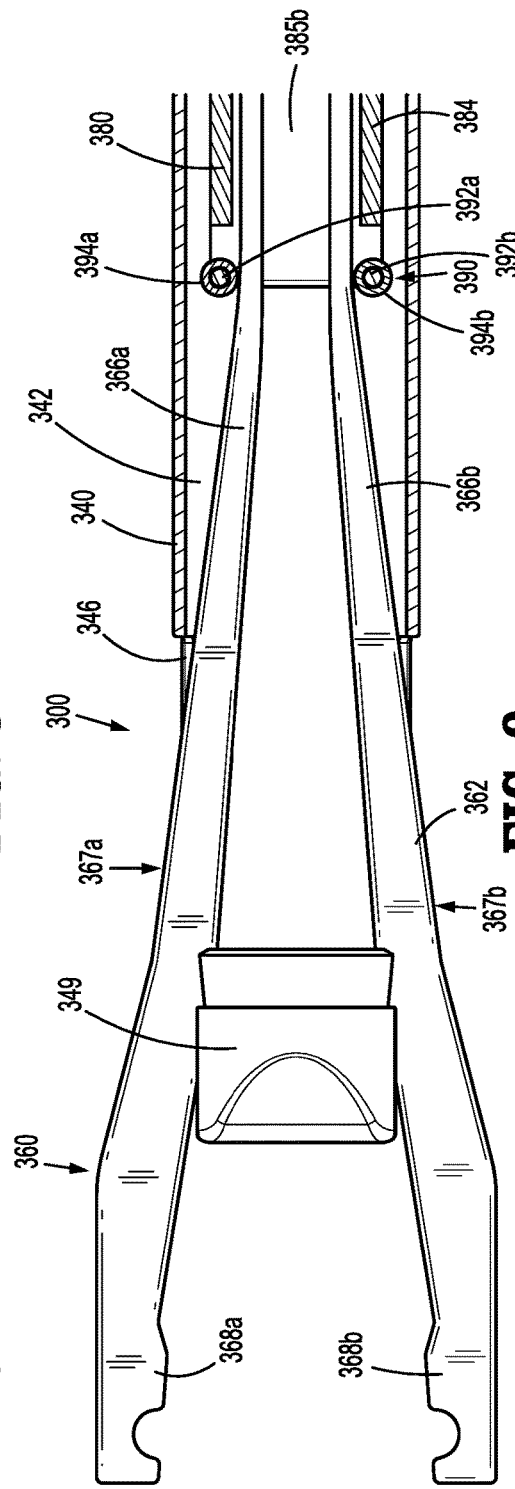

ELONGATED ASSEMBLIES FOR SURGICAL CLIP APPLIERS AND SURGICAL CLIP APPLIERS INCORPORATING THE SAME

CROSS-REFERENCE TO RELATED APPLICATION

This application claims the benefit of and priority to U.S. Provisional Patent Application No. 62/717,952 filed Aug. 13, 2018, the entire disclosure of which is incorporated by reference herein.

BACKGROUND

Technical Field

The present disclosure relates to surgical instruments. More particularly, the present disclosure relates to elongated assemblies for surgical clip appliers and surgical clip appliers including the same.

Description of Related Art

Surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures.

Endoscopic surgical clip appliers having various sizes (e.g., diameters), that are configured to apply a variety of diverse surgical clips, are also known in the art, and are capable of applying a single or multiple surgical clips during an entry to the body cavity. Such surgical clips are typically fabricated from a biocompatible material and are usually compressed over tissue. Once applied to tissue, the compressed surgical clip terminates the flow of fluid therethrough.

SUMMARY

As detailed herein and shown in the drawing figures, as is traditional when referring to relative positioning on a surgical instrument, the term "proximal" refers to the portion of the apparatus or component thereof which is closer to the user and the term "distal" refers to the portion of the apparatus or component thereof which is further away from the user. Further, to the extent consistent, any or all of the aspects and features detailed herein may be used in conjunction with any or all of the other aspects and features detailed herein.

Provided in accordance with aspects of the present disclosure is an elongated assembly of a surgical clip applier including an outer shaft, an end effector assembly, and an inner drive sleeve. The end effector assembly is disposed partially within and extends distally from the outer shaft. The end effector assembly includes first and second spaced-apart arms and first and second jaws disposed at free ends of the first and second spaced-apart arms, respectively.

The inner drive sleeve is disposed within the outer shaft and includes a bearing assembly slidably disposed about the end effector assembly. The bearing assembly includes a first bearing roller positioned adjacent the first spaced-apart arm and a second bearing roller positioned adjacent the second spaced-apart arm. Sliding of the bearing assembly from a proximal position to a distal position rolls the first and second bearing rollers along the first and second spaced-apart arms, respectively, to urge the first and second spaced-apart arms towards one another, thereby moving the first and second jaws from a spaced-apart position to an approximated position to apply a surgical clip about tissue disposed between the first and second jaws.

In an aspect of the present disclosure, the first and second bearing rollers are rotatably mounted on first and second posts disposed on opposite sides of the inner drive sleeve. The first and second posts, in aspects, may be disposed at the distal end of the inner drive sleeve. Additionally or alternatively, in aspects, the inner drive sleeve may define a rectangular cross-sectional configuration including opposed narrow sides and opposed wide sides wherein the first and second posts are mounted along the narrow sides.

In another aspect of the present disclosure, the first and second bearing rollers are disposed in parallel, spaced-apart relation relative to one another with the first and second spaced-apart arms disposed therebetween.

In still another aspect of the present disclosure, the first and second spaced-apart arms define inwardly-facing surfaces and outwardly-facing surfaces wherein the first and second bearing rollers are configured to roll along the outwardly-facing surfaces of the first and second spaced-apart arms, respectively. In such aspects, the outwardly-facing surfaces of the first and second spaced-apart arms may define generally smooth, flat configurations.

In yet another aspect of the present disclosure, the first and second spaced-apart arms are resiliently flexible from an at-rest position to a flexed position in response to movement of the bearing assembly from the proximal position to the distal position to thereby move the first and second jaws from the spaced-apart position to the approximated position.

In still yet another aspect of the present disclosure, the first and second spaced-apart arms are joined to one another via a proximal base that is fixed relative to the outer shaft.

In another aspect of the present disclosure, the elongated assembly further includes a proximal hub disposed at a proximal end of the outer shaft and configured to releasably engage the elongated assembly with a handle assembly.

Also provided in accordance with aspects of the present disclosure is a surgical clip applier including a handle assembly including a housing and a trigger operably coupled to the housing, and an elongated assembly extending distally from the handle assembly. The elongated assembly may include any of the aspects and features detailed above or otherwise herein.

BRIEF DESCRIPTION OF THE DRAWINGS

Aspects and features of the present disclosure are described in detail with reference to the drawing figures wherein like reference numerals identify similar or identical structural elements and:

FIG. 4 is a side view of the surgical clip applier with portions removed;

FIG. 5 is a side, perspective view, with portions shown transparent, of a distal portion of the elongated assembly of FIG. 1;

FIG. 7A is a longitudinal, cross-sectional view of the distal portion of the elongated assembly of FIG. 1;

FIG. 7B is an enlarged, longitudinal, cross-sectional view of the area of detail indicated as "7B" in FIG. 7A;

FIG. 8 is a perspective, partial cut-away view of the distal portion of another elongated assembly similar to the elongated assembly of FIG. 1 and configured for use with the handle assembly of FIG. 1; and FIG. 9 is a longitudinal, top cross-sectional view of the distal portion of the elongated assembly of FIG. 8.

DETAILED DESCRIPTION

Figure 1:
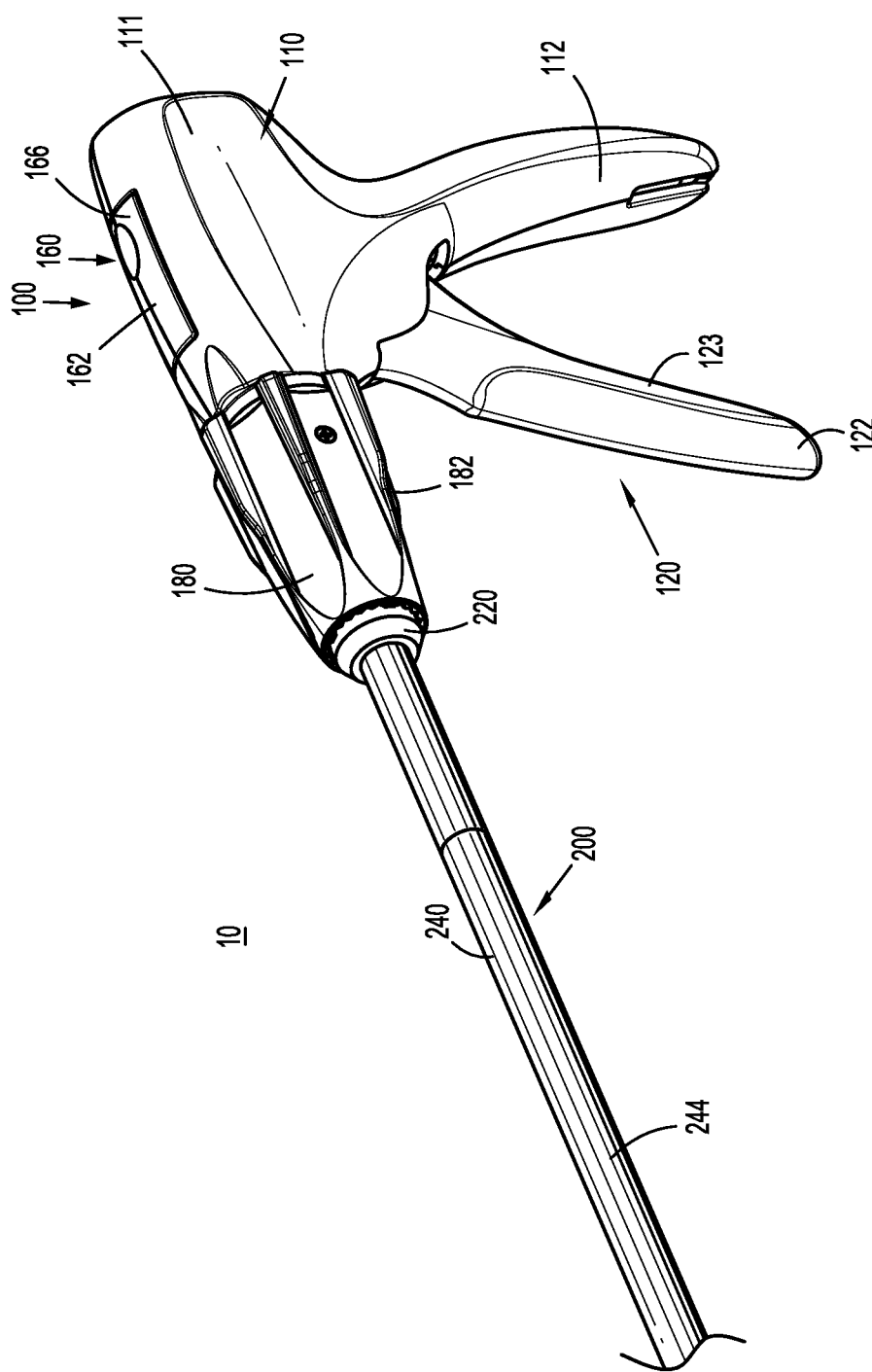
FIG. 1 is a front, perspective view of a surgical clip applier provided in accordance with the present disclosure including a handle assembly having an elongated assembly engaged therewith.
Figure 2:
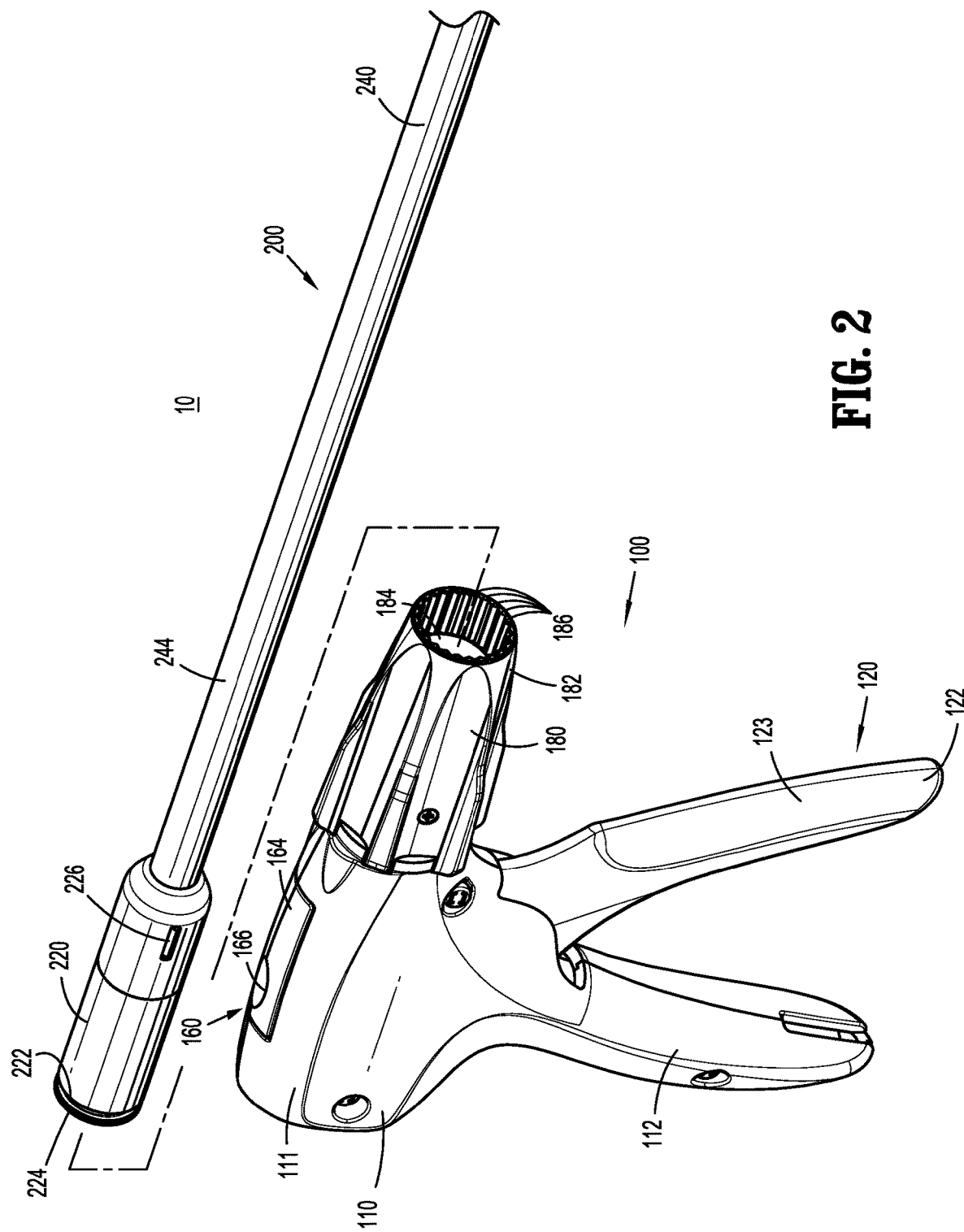
FIG. 2 is front, perspective view of the surgical clip applier with the elongated assembly removed from the handle assembly.
Figure 3A:
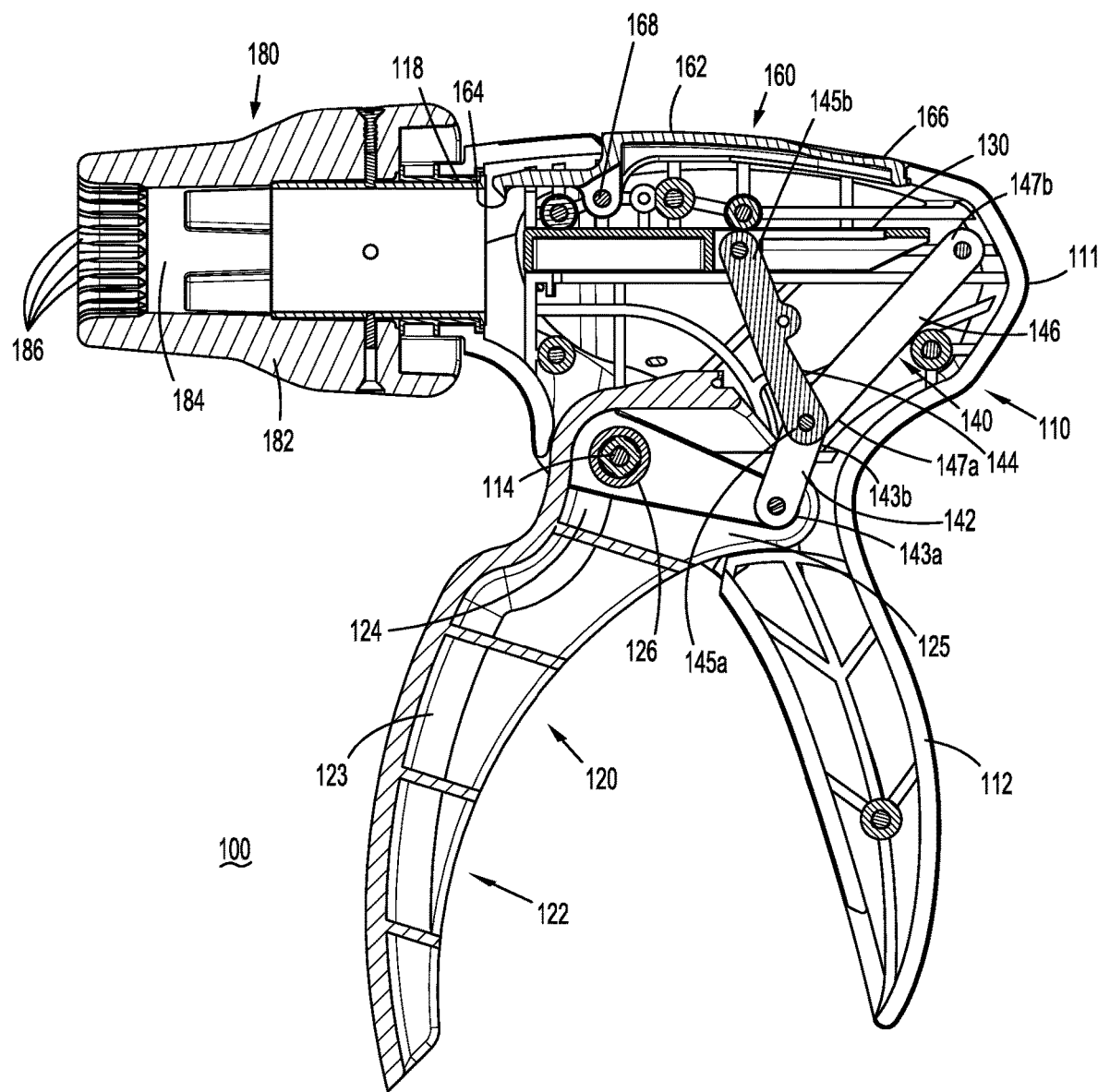
FIG. 3A is an enlarged, side view of the handle assembly of the surgical clip applier with portions removed to illustrate the internal components and features therein, wherein the trigger is disposed in an un-actuated position.
Figure 3B:
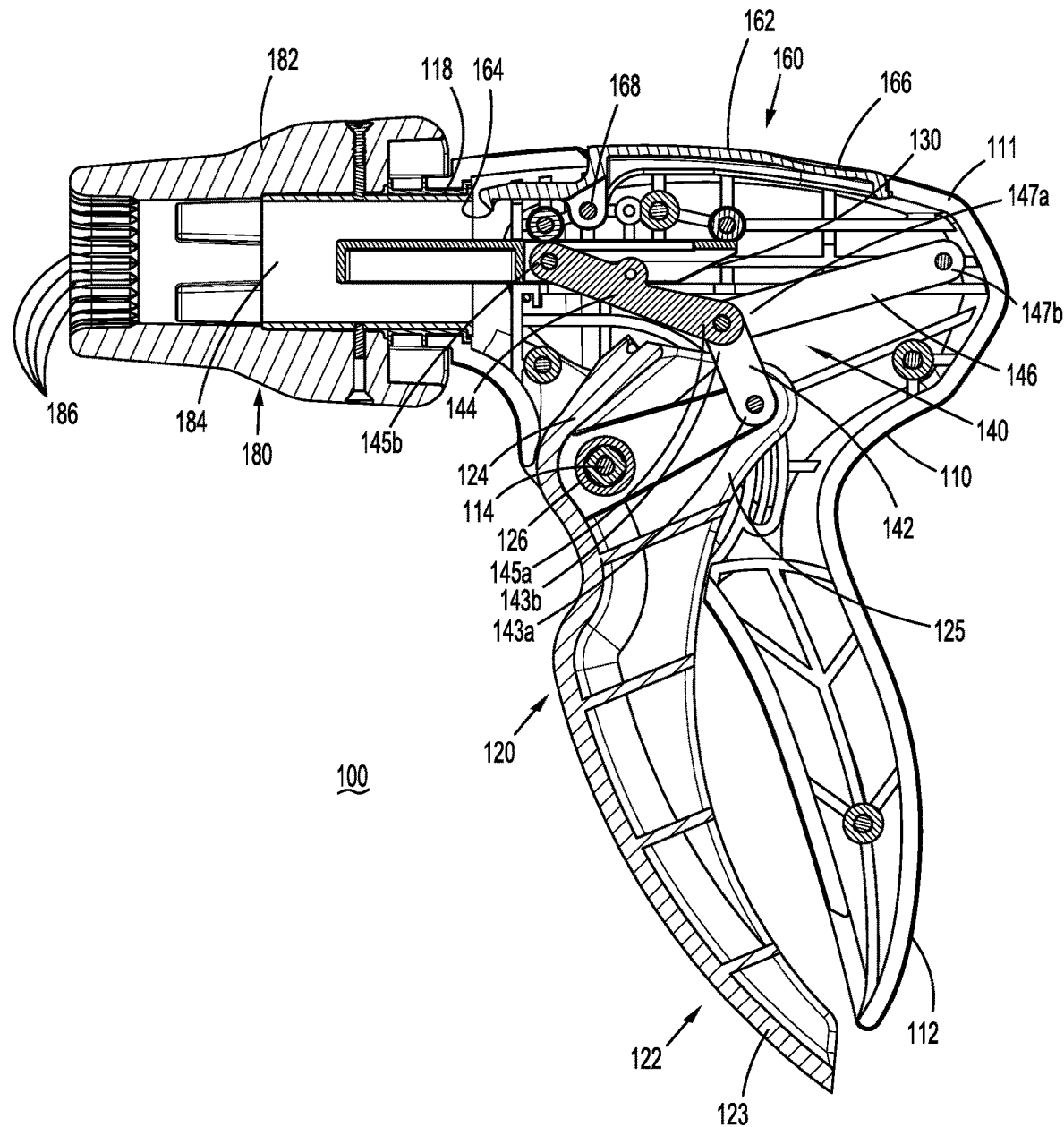
FIG. 3B is an enlarged, side view of the handle assembly of the surgical clip applier with portions removed to illustrate the internal components and features therein, wherein the trigger is disposed in an actuated position.

Turning to FIGS. 1-4, a surgical clip applier embodying the aspects and features of the present disclosure is shown generally identified by reference numeral 10. Surgical clip applier 10 generally includes a handle assembly 100 and an elongated assembly 200 selectively connectable to handle assembly 100. Handle assembly 100 is configured to operate elongated assembly 200 upon connection thereto, and may be configured as a sterilizable, reusable component such that handle assembly 100 may be repeatedly used with different and/or additional elongated assemblies 200 during the course of one or more surgical procedures. Elongated assembly 200 may be configured as single-use disposable component, limited-use disposable component, or reusable component, depending upon a particular purpose.

Handle assembly 100 generally includes a housing 110, an actuation mechanism 120 operably associated with housing 110, a latch assembly 160 operably associated with housing 110, and a rotating receiver assembly 180 operably coupled to a distal portion of housing 110. Housing 110 of handle assembly 100 supports and/or encloses the operating components of handle assembly 100 and defines a body portion 111 and a fixed handle portion 112 depending from body portion 111. Body portion 111 of housing 110 includes an internal pivot post 114 extending transversely within body portion 111 and a distal opening 118 through which a proximal end portion of elongated assembly 200 extends when elongated assembly 200 is engaged with handle assembly 100.

Actuation mechanism 120 is operably supported by housing 110 and includes a trigger 122, a drive bar 130, and a linkage assembly 140. Trigger 122 includes a grasping portion 123, an intermediate pivot portion 124, and a proximal extension 125. Grasping portion 123 of trigger 122 extends downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and defines a pivot aperture 126 that is configured to receive pivot post 114 of housing 110 so as to enable pivoting of trigger 122 about pivot post 114 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension 125 of trigger 122 is disposed on an opposite side of intermediate pivot portion 124 and, thus, pivot post 114, as compared to grasping portion 123 of trigger 122. As such, pivoting of grasping portion 123 to rotate in one direction, e.g., proximally towards fixed handle portion 112, pivots proximal extension 125 to rotate in the opposite direction, e.g., distally.

Linkage assembly 140 includes a first linkage 142, a second linkage 144, and a third linkage 146. First linkage 142 is pivotably coupled to proximal extension 125 of trigger 122 towards a first end 143a of first linkage 142. Second and third linkages 144, 146, respectively, are each pivotably coupled to a second end 143b of first linkage 142 at respective first ends 145a, 147a of second and third linkages 144, 146. A second end 145b of second linkage 144 is pivotably coupled to drive bar 130, while a second end 147b of third linkage 146 is pivotably coupled to body portion 111 of housing 110. Thus, the pivot point between first linkage 142 and proximal extension 125 of trigger 122, the pivot point between first linkage 142 and second and third linkages 144, 146, respectively, and the pivot point between second linkage 144 and drive bar 130 are movable pivot points (e.g., movable relative to housing 110), while the pivot point between third linkage 146 and housing 110 is a fixed pivot point (e.g., fixed relative to housing 110).

Upon actuation of trigger 122, e.g., proximal pivoting of grasping portion 123 of trigger 122, proximal extension 125 is moved in a counter-clockwise direction (from the orientation illustrated in FIG. 3A), thereby urging first linkage 142 towards drive bar 130. This movement of first linkage 142 towards drive bar 130, in turn, urges first ends 145a, 147a of second and third linkages 144, 146, respectively, towards drive bar 130 to, in turn, urge second end 145b of second linkage 144 distally such that drive bar 130 is translated distally through body portion 111 of housing 110. A biasing spring (not shown) may be provided to bias trigger 122 towards an un-actuated position, thereby biasing drive bar 130 proximally.

Drive bar 130 is slidably disposed within body portion 111 of housing 110 in longitudinal alignment with proximal portion 282 of inner drive sleeve 280 of elongated assembly 200 (see FIG. 4) when elongated assembly 200 is engaged with handle assembly 100 such that distal sliding of drive bar 130 through body portion 111 of housing urges drive bar 130 into contact with proximal portion 282 of inner drive sleeve 280 to thereby translate inner drive sleeve 280 distally, e.g., to apply, form or close a surgical clip supported at end effector assembly 260 of elongated assembly 200, as detailed below.

Latch assembly 160 is configured to facilitate releasable locking engagement of elongated assembly 200 with handle assembly 100. Latch assembly 160, more specifically, includes a pivoting lever arm 162 operably disposed on and extending into body portion 111 of housing 110. Lever arm 162 includes an engagement finger 164 disposed towards one end thereof and a manipulatable portion 166 disposed towards the other end thereof with a pivot portion 168 disposed therebetween. Thus, upon depression of manipulatable portion 166 into housing 110 from a locked position to an unlocked position, engagement finger 164 is withdrawn upwardly and, upon release of manipulatable portion 166 and return thereof to the locked position, engagement finger 164 is returned downwardly. A torsion spring (not shown) disposed about pivot portion 168, or other suitable biasing spring in any suitable position, may be provided to bias lever arm 162 towards the locked position, although other configurations are also contemplated.

Rotating receiver assembly 180 is configured to receive a proximal end portion of elongated assembly 200 and to enable selective rotation thereof relative to housing 110. Rotating receiver assembly 180 includes a rotation knob 182 rotatably coupled to body portion 111 of housing 110 and extending distally therefrom. Rotation knob 182 defines a lumen 184 extending therethrough in communication with distal opening 118 of body portion 111 of housing 110 to enable insertion of a proximal portion of elongated assembly 200 therethrough and into operable engagement within housing 110. Rotation knob 184 defines channels 186 disposed on an interior surface thereof and arranged annularly about lumen 184 to enable rotatable coupling of elongated assembly 200 therewith, as detailed below.

Figure 6:
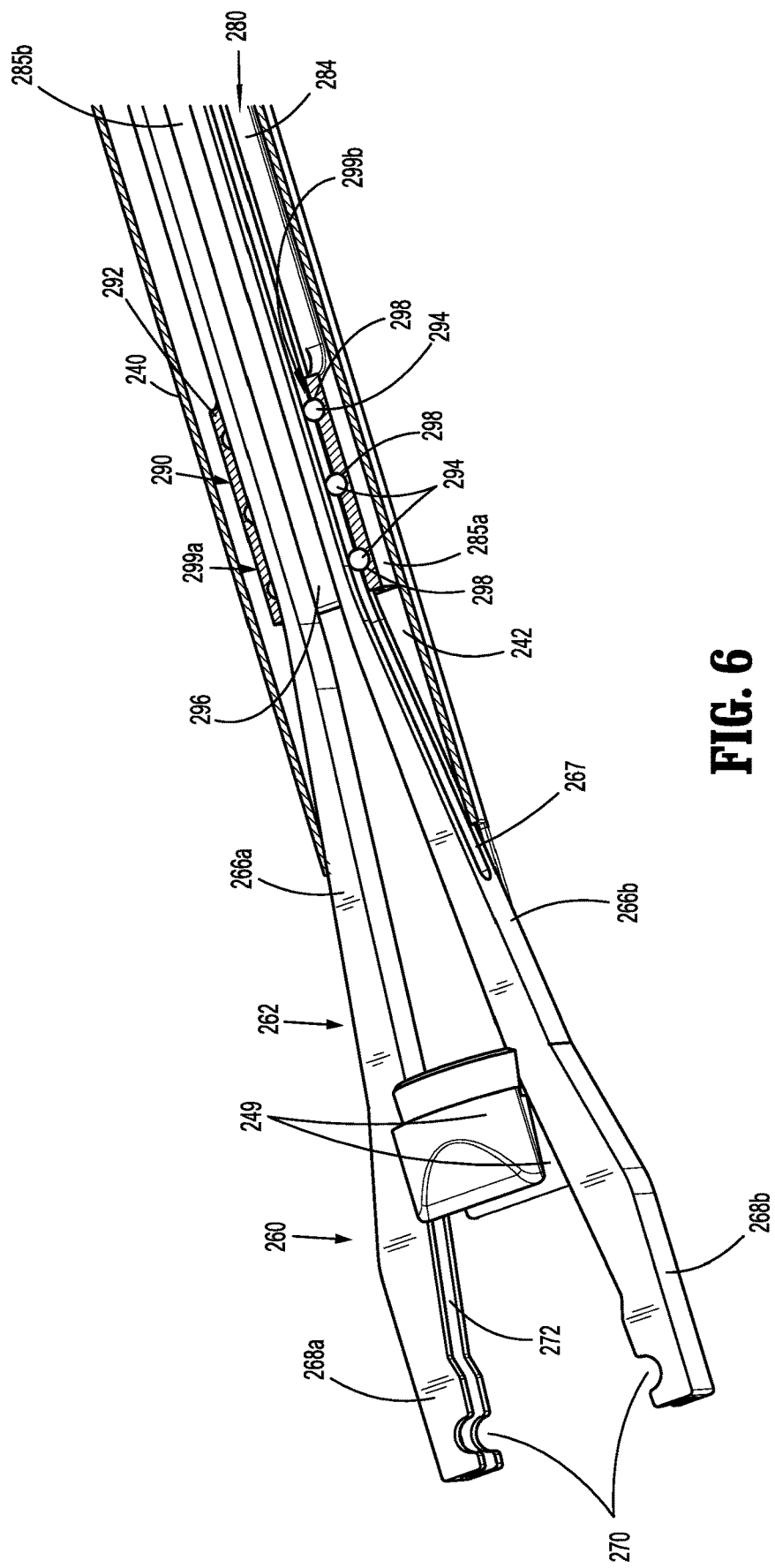
FIG. 6 is a side, perspective, partial longitudinal cross-sectional view of the distal portion of the elongated assembly of FIG. 1.

With reference to FIGS. 4-7B, elongated assembly 200 generally includes a proximal hub 220 (FIG. 4), an elongated shaft 240 extending distally from proximal hub 220, an end effector assembly 260 disposed towards a distal end portion of elongated shaft 240, and an inner drive sleeve 280 slidably disposed through proximal hub 220 and elongated shaft 240 and configured for operable coupling between handle assembly 100 and end effector assembly 260 when elongated assembly 200 is engaged with handle assembly 100 to enable firing of a surgical clip (not shown) about tissue. Elongated assembly 200 further includes a bearing assembly 290 (FIGS. 6-7B) configured to facilitate movement of inner drive sleeve 280 about end effector assembly 260 to thereby facilitate firing a surgical clip (not shown) about tissue, as detailed below.

Proximal hub 220 is configured for insertion through lumen 184 of rotation knob 182 and into body portion 111 of housing 110. Proximal hub 220 defines an annular recess 222 towards the proximal end thereof and a chamfered proximal edge 224. Thus, upon insertion of proximal hub 220 through lumen 184 of rotation knob 182 and into body portion 111 of housing 110, chamfered proximal edge 224 cams engagement finger 164 of latch assembly 160 over the outer surface of proximal hub 220 until engagement finger 164 is disposed in alignment with annular recess 222, wherein engagement finger 164 falls into engagement within annular recess 222 to engage proximal hub 220 and, thus, elongated assembly 200, with handle assembly 100. As can be appreciated, in order to disengage and remove elongated assembly 200 from handle assembly 100, manipulatable portion 166 of latch assembly 160 is depressed into housing 110 to withdraw engagement finger 164 from annular recess 222 and enable elongated assembly 200 to be pulled distally and removed from handle assembly 100. Proximal hub 220 may further include a lock tab 226 extending along a portion of the length thereof and configured for receipt within one of the channels 186 defined within rotation knob 182 to rotationally fix elongated assembly 200 relative to rotation knob 182 upon insertion therein.

Elongated shaft 240 extends distally from proximal hub 220 and defines a longitudinal lumen 242 extending therethrough. Elongated shaft 240 further includes a body 244 and a bifurcated distal portion 246 including a pair of radially-opposed flanges 248 extending distally from body 244. Opposed flanges 248 define tissue stops 249 configured to inhibit passage of tissue into the space defined therebetween.

Continuing with reference to FIGS. 4-7B, end effector assembly 260 of elongated assembly 200 is formed as a monolithic component of a single piece of material (see FIG. 7A), e.g., via stamping or other suitable manufacturing process (although multi-part configurations and/or other manufacturing techniques are also contemplated), and includes a jaws component 262 having a proximal base 264, a pair of spaced-apart arms 266a, 266b extending distally from proximal base 264, and a jaw 268a, 268b disposed at the free distal end of each arm 266a, 266b, respectively.

Proximal base 264 of jaws component 262 defines pair of apertures 265 extending transversely therethrough and in longitudinal alignment with one another, although greater or fewer apertures or otherwise arranged apertures are also contemplated. Apertures 265 are configured for receipt of pins 250, 252 which extend transversely through elongated shaft 240 and at least partially into opposed pairs of apertures 254, 256, respectively, defined transversely through elongated shaft 240. The portions of pins 250, 252 extending into or through apertures 254, 256 may be welded to elongated shaft 240 or otherwise engaged thereto to fix pins 250, 252 and, thus, proximal base 264 of jaws component 262 relative to elongated shaft 240.

Spaced-apart arms 266a, 266b of jaws component 262 extend distally from proximal base 264 to jaws 268a, 268b, respectively, and are resiliently flexible (or otherwise movable) from an at-rest position, wherein spaced-apart arms 266a, 266b are angled apart from one another to define an increasing distance therebetween in the proximal-to-distal direction, to a flexed position, wherein spaced-apart arms 266a, 266b are closer to one another and disposed in a more-parallel orientation or angled towards one another. Spaced-apart arms 266a, 266b are oriented 90 degrees offset from flanges 248 of elongated shaft 240 to enable the portions of spaced-apart arms 266a, 266b disposed between flanges 248 to extend outwardly beyond the outer dimension of elongated shaft 240 in the at-rest position thereof without interference from flanges 248. This configuration also positions tissue stops 249 on the lateral sides of spaced-apart arms 266a, 266 to inhibit tissue ingress into the space defined between spaced-apart arms 266a, 266b. In embodiments, arms 266a, 266b may define longitudinally-extending grooves 267 on the opposed exterior surfaces thereof along at least a portion of the longitudinal length thereof. As detailed below, each groove 267 is configured to receive one or more ball bearings 294 and serves as a guide track for ball bearings 294 along arms 266a, 266b as inner drive sleeve 280 and bearing assembly 290 thereof move about jaws component 262.

Jaws 268a, 268b, as noted above, are disposed at the free distal ends of spaced-apart arms 266a, 266b, respectively. Jaws 268a, 268b may define transverse notches 270, longitudinal slots 272, and/or other suitable features to facilitate retention of legs of a surgical clip (not shown) therein. Jaws 268a, 268b are moved from a spaced-apart position to an approximated position upon movement of spaced-apart arms 266a, 266b from the at-rest position to the flexed position to thereby form a surgical clip held between jaws 268a, 268b about tissue disposed between jaws 268a, 268b. End effector assembly 260, in embodiments, may be configured to form surgical clips similar to those shown and described in U.S. Pat. No. 4,834,096, the entire contents of which is hereby incorporated herein by reference.

Inner drive sleeve 280 defines a proximal portion 282 (FIG. 4) and a distal portion 284. Proximal portion 282 of inner drive sleeve 280 is configured for positioning adjacent a distal end of drive bar 130 of handle assembly 100 when elongated assembly 200 is engaged with handle assembly 100 (see FIG. 4) such that, as noted above, distal translation of drive bar 130 through housing 110 (e.g., in response to actuation of trigger 122), urges drive bar 130 into contact with proximal portion 2828 of inner drive sleeve 280 to translate inner drive sleeve 280 distally through elongated shaft 240 of elongated assembly 200. In embodiments, proximal portion 282 of inner drive sleeve 280 may be configured to releasably engage the distal end of drive bar 130.

Referring still to FIGS. 4-7B, distal portion 284 of inner drive sleeve 280 includes bearing assembly 290 disposed therein towards the distal end thereof, is slidably disposed about at least a proximal portion of jaws component 262 of end effector assembly 260, and defines a rectangular transverse cross-sectional configuration having a pair of narrow sides 285a and a pair of wide sides 285b. Opposed longitudinally-extending slots 286 are defined through wide sides 285b of distal portion 284 of inner drive sleeve 280 in alignment with one another. Slots 286 enable passage of pins 250, 252 therethrough while still enabling sliding of distal portion 284 of inner drive sleeve 280 through elongated shaft 240 and about end effector assembly 260. Distal portion 284 of inner drive sleeve 280 is oriented such that spaced-apart arms 266a, 266b of jaws component 262 are disposed adjacent opposed narrow sides 285a of distal portion 284 with, in embodiments, the width of opposed narrow sides 285a generally approximating the width of spaced-apart arms 266a, 266b to inhibit relative lateral motion between spaced-apart arms 266a, 266b, thereby inhibiting splay between jaws 268a, 268b.

Wide sides 285b of distal portion 284 of inner drive sleeve 280 define heights greater than the minimum distance between spaced-apart arms 266a, 266b but less than the maximum distance between spaced-apart arms 266a, 266b such that distal sliding of distal portion 284 of inner drive sleeve 280 about jaws component 262, e.g., in response to actuation of trigger 122 (FIGS. 1-4), moves bearing assembly 290 about the exterior surfaces of spaced-apart arms 266a, 266b to urge spaced-apart arms 266a, 266b towards one another from the at-rest position towards the flexed position, thereby moving jaws 268a, 268b from the spaced-apart position towards the approximated position to form or close a surgical clip positioned therebetween about tissue disposed between jaws 268a, 268b. Upon release or return of trigger 122 (FIG. 1), inner drive sleeve 280 is returned proximally, allowing spaced-apart arms 266a, 266b to resiliently return towards the at-rest position, thereby returning jaws 268a, 268b towards the spaced-apart position to enable loading of a subsequent surgical clip for formation or closing about tissue. A biasing spring (not shown) associated with elongated assembly 200 may be provided to bias inner drive sleeve 280 proximally such that, upon release of trigger 122 (FIGS. 1-4), inner drive sleeve 280 is returned proximally. Other suitable biasing configurations are also contemplated.

Bearing assembly 290, as noted above, is disposed within distal portion 284 of inner drive sleeve 280 and is configured to move about the exterior surfaces of spaced-apart arms 266a, 266b to urge spaced-apart arms 266a, 266b from the at-rest position towards the flexed position. Bearing assembly 290 includes a ferrule 292 and a plurality of ball bearings 294. Ferrule 292 is engaged with, formed as part of, or otherwise disposed within distal portion 284 of inner drive sleeve 280 towards the distal end thereof. Ferrule 292 defines a longitudinal lumen 296 extending therethrough that receives spaced-apart arms 266a, 266b of jaws component 262 and, similarly as with distal portion 284 of inner drive sleeve 280, defines a rectangular cross-sectional configuration of like orientation.

Ball bearings 294 are captured by ferrule 292 but remain free to rotate relative to ferrule 292 and, thus inner drive sleeve 280. A portion of each ball bearing 294 protrudes inwardly through a respective opening 298 defined on the interior surface (surrounding longitudinal lumen 296) of ferrule 292 and into longitudinal lumen 296. Alternatively, ball bearings 294 may be captured by ferrule 292 in any other suitable manner such that ball bearings 294 remain rotatable relative to ferrule 292 and a portion of each ball bearing 294 extends into longitudinal lumen 296. In other embodiments, ball bearings are captured cooperatively between ferrule 292 and jaws component 262.

Ball bearings 294 may be arranged in any suitable manner such as, for example, in two groups wherein a first group 299a of ball bearings 294 (including one or more ball bearings 294) is aligned longitudinally along a first side of bearing assembly 290 and a second group 299b of ball bearings 294 (including one or more other ball bearings 294) is aligned longitudinally along a second, opposite side of bearing assembly 290 such that ball bearings 294 protrude into longitudinal lumen 296 from opposing sides thereof. More specifically, first group 299a of ball bearings 294 may be arranged along one of the narrow sides 285a of inner drive sleeve 280 while second group 299b of ball bearings 294 is arranged along the opposite narrow side 285a of inner drive sleeve 280. In embodiments, first and second groups 299a, 299b each include a plurality of ball bearings 294 aligned longitudinally or otherwise arranged. In embodiment where spaced-apart arms 266a, 266b of jaws component 262 define longitudinally-extending grooves 267, the first group 299a of ball bearings 294 may be received within the groove 267 of one of the spaced-apart arms 266a while the second group 299b of ball bearings 294 is received within the groove 267 of the other spaced-apart arm 266b.

As noted above, in use, distal sliding of distal portion 284 of inner drive sleeve 280 about jaws component 262, e.g., in response to actuation of trigger 122 (FIG. 1), moves bearing assembly 290 about the exterior surfaces of spaced-apart arms 266a, 266b to urge spaced-apart arms 266a, 266b towards one another from the at-rest position towards the flexed position to form or close a surgical clip positioned between jaws 268a, 268b about tissue. More specifically, as distal portion 284 of inner drive sleeve 280 is moved distally about spaced-apart arms 266a, 266b, ball bearings 294 roll along the exterior surface of spaced-apart arms 266a, 266b and relative to ferrule 292 (and, thus, inner drive sleeve 280) to urge spaced-apart arms 266a, 266b towards one another. Ball bearings 294, by rolling along spaced-apart arms 266a, 266b and relative to ferrule 292, help reduce friction during actuation, thereby enabling a smoother actuation, reducing the actuation force, enabling greater tactile feedback at trigger 122 (FIG. 1) during actuation, and increasing longevity. In addition, the receipt of first and second groups 299a, 299b of ball bearings 294 within grooves 267 of spaced-apart arms 266a, 266b, respectively, establishes a guide track to help maintain alignment of arms 266a, 266b and, thus, jaws 268a, 268b during actuation.

Turning to FIGS. 8 and 9, another embodiment of an elongated assembly provided in accordance with the present disclosure and configured for use with handle assembly 100 (FIGS. 1-3B) as part of a surgical clip applier 10 (FIG. 1) is shown generally identified by reference numeral 300. Elongated assembly 300 may be similar to or include any of the features of elongated assembly 200 (FIGS. 1-7B), except as specifically contradicted below.

Elongated assembly 300 generally includes a proximal hub (not shown, similar to proximal hub 220 of elongated assembly 200 (FIGS. 4-5)), an elongated shaft 340 extending distally from the proximal hub, an end effector assembly 360 disposed towards a distal end portion of elongated shaft 340 and extending distally therefrom, and an inner drive sleeve 380 slidably disposed through the proximal hub and elongated shaft 340 and configured for operable coupling between handle assembly 100 (FIG. 1) and end effector assembly 360 when elongated assembly 300 is engaged with handle assembly 100 (FIG. 1) to enable firing of a surgical clip (not shown) about tissue. Elongated assembly 300 further includes a bearing assembly 390 configured to facilitate movement of inner drive sleeve 380 about end effector assembly 360 to thereby facilitate firing a surgical clip (not shown) about tissue, as detailed below.

Elongated shaft 340 extends distally from the proximal hub and defines a longitudinal lumen 342 extending therethrough. Elongated shaft 340 further includes a bifurcated distal portion 346 including a pair of tissue stops 349 similarly as detailed above with respect to elongated assembly 200 (FIGS. 4-5).

End effector assembly 360 of elongated assembly 300 is similar to end effector assembly 260 of elongated assembly 200 (FIGS. 4-7B) and generally includes a jaws component 362 having a proximal base (not shown), a pair of spaced-apart arms 366a, 366b extending distally from the proximal base, and a jaw 368a, 368b disposed at the free distal end of each arm 366a, 366b, respectively. Spaced-apart arms 366a, 366b define generally smooth and flat (within manufacturing, material, and use tolerances) opposed exterior surfaces 367a, 367b.

Inner drive sleeve 380 defines a proximal portion (not shown, similar to proximal portion 282 of inner drive sleeve 280 (FIG. 4)) and a distal portion 384 and is similar to inner drive sleeve 280 (FIG. 4) except for the configuration of the respective bearing assemblies 290 (FIGS. 7A-7B), 390 thereof, as detailed below. Distal portion 384 of inner drive sleeve 380 includes bearing assembly 390 disposed towards and, in embodiments, at the distal end thereof. Distal portion 384 of inner drive assembly 380 is slidably disposed about at least a proximal portion of jaws component 362 of end effector assembly 360, and defines a rectangular transverse cross-sectional configuration having a pair of narrow sides 385a and a pair of wide sides 385b. Distal portion 384 of inner drive sleeve 380 is oriented such that spaced-apart arms 366a, 366b of jaws component 362 are disposed adjacent opposed narrow sides 385a of distal portion 384.

Bearing assembly 390, as noted above, is disposed towards and, in embodiments, at the distal end of distal portion 384 of inner drive sleeve 380 and includes a pair of spaced-apart posts 392a, 392b and a pair of bearing rollers 394a, 394b, with each bearing roller 394a, 394b disposed about and rotatable relative to one of the posts 392a, 392b, respectively. Posts 392a, 392b are mounted adjacent and extend along narrow sides 385a of distal portion 384 of inner drive sleeve 380 and extend between wide sides 385b of distal portion 384 of inner drive sleeve 380 in generally parallel and spaced-apart relation relative to one another. Bearing rollers 394a, 394b are rotatably disposed about posts 392a, 392b and similarly extend along narrow sides 385a of distal portion 384 of inner drive sleeve 380 and between wide sides 385b of distal portion 384 of inner drive sleeve 380 in generally parallel and spaced-apart relation relative to one another. Jaws component 362 extends between the bearing rollers 394a, 394b.

As a result of the above-detailed position and orientation of bearing rollers 394a, 394b, spaced-apart arms 366a, 366b of jaws component 362 of end effector assembly 360 extend between bearing rollers 394a, 394b with opposed exterior surfaces 367a, 367b of spaced-apart arms 366a, 366b abutting or, in some positions, in close proximity to bearing rollers 394a, 394b, respectively. In use, distal sliding of distal portion 384 of inner drive sleeve 380 about jaws component 362, e.g., in response to actuation of trigger 122 (FIG. 1), moves bearing assembly 390 about the exterior surfaces 367a, 367b of spaced-apart arms 366a, 366b to urge spaced-apart arms 366a, 366b towards one another from the at-rest position towards the flexed position, thereby moving jaws 368a, 368b from the spaced-apart position towards the approximated position to form or close a surgical clip positioned therebetween about tissue disposed between jaws 368a, 368b. More specifically, as distal portion 384 of inner drive sleeve 380 is slid distally, bearing rollers 394a, 394b contact and roll along opposed exterior surfaces 367a, 367b of spaced-apart arms 366a, 366b (while rotating about posts 392a, 392b relative to inner drive sleeve 380) to urge spaced-apart arms 366a, 366b towards one another. Bearing rollers 394a, 394b, by rolling along spaced-apart arms 366a, 366b, help reduce friction during actuation, thereby enabling a smoother actuation, reducing the actuation force, enabling greater tactile feedback at trigger 122 (FIG. 1) during actuation, and increasing longevity.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An elongated assembly of a surgical clip applier, comprising:
    an outer shaft;
    an end effector assembly disposed partially within and extending distally from the outer shaft, the end effector assembly including first and second spaced-apart arms and first and second jaws disposed at free ends of the first and second spaced-apart arms, respectively;
    an inner drive sleeve disposed within the outer shaft; and
    a bearing assembly slidably disposed about the end effector assembly, the bearing assembly including a first bearing roller positioned adjacent the first spaced-apart arm and a second bearing roller positioned adjacent the second spaced-apart arm, wherein at least a portion of the first bearing roller extends distally beyond the inner drive sleeve, wherein sliding of the bearing assembly from a proximal position to a distal position rolls the first and second bearing rollers along the first and second spaced-apart arms, respectively, to urge the first and second spaced-apart arms towards one another, thereby moving the first and second jaws from a spaced-apart position to an approximated position to apply a surgical clip about tissue disposed between the first and second jaws.

2. The elongated assembly according to claim 1, wherein the first and second bearing rollers are rotatably mounted on first and second posts disposed on opposite sides of the inner drive sleeve.

3. The elongated assembly according to claim 2, wherein the first and second posts are disposed at a distal end of the inner drive sleeve.

4. The elongated assembly according to claim 2, wherein the inner drive sleeve defines a rectangular cross-sectional configuration including opposed narrow sides and opposed wide sides, and wherein the first and second posts are mounted along the narrow sides.

5. The elongated assembly according to claim 1, wherein the first and second bearing rollers are disposed in parallel, spaced-apart relation relative to one another with the first and second spaced-apart arms disposed therebetween.

6. The elongated assembly according to claim 1, wherein the first and second spaced-apart arms define inwardly-facing surfaces and outwardly-facing surfaces, the first and second bearing rollers configured to roll along the outwardly-facing surfaces of the first and second spaced-apart arms, respectively.

7. The elongated assembly according to claim 6, wherein the outwardly-facing surfaces of the first and second spaced-apart arms define generally smooth, flat configurations.

8. The elongated assembly according to claim 1, wherein the first and second spaced-apart arms are resiliently flexible from an at-rest position to a flexed position in response to movement of the bearing assembly from the proximal position to the distal position to thereby move the first and second jaws from the spaced-apart position to the approximated position.

9. The elongated assembly according to claim 1, wherein the first and second spaced-apart arms are joined to one another via a proximal base, the proximal base fixed relative to the outer shaft.

10. The elongated assembly according to claim 1, further comprising a proximal hub disposed at a proximal end of the outer shaft, the proximal hub configured to releasably engage the elongated assembly with a handle assembly.

11. A surgical clip applier, comprising:
a handle assembly including a housing and a trigger operably coupled to the housing;
an elongated assembly extending distally from the handle assembly, the elongated assembly including:
an outer shaft;
an end effector assembly disposed partially within and extending distally from the outer shaft, the end effector assembly including first and second spaced-apart arms and first and second jaws disposed at free ends of the first and second spaced-apart arms, respectively;
an inner drive sleeve disposed within the outer shaft; and
a bearing assembly slidably disposed about the end effector assembly, the bearing assembly including a first bearing roller positioned adjacent the first spaced-apart arm and a second bearing roller positioned adjacent the second spaced-apart arm, wherein at least a portion of the first bearing roller extends distally beyond the inner drive sleeve, wherein actuation of the trigger slides the bearing assembly from a proximal position to a distal position whereby the first and second bearing rollers roll along the first and second spaced-apart arms, respectively, to urge the first and second spaced-apart arms towards one another, thereby moving the first and second jaws from a spaced-apart position to an approximated position to apply a surgical clip about tissue disposed between the first and second jaws.

12. The surgical clip applier according to claim 11, wherein the first and second bearing rollers are rotatably mounted on first and second posts disposed on opposite sides of the inner drive sleeve.

13. The surgical clip applier according to claim 12, wherein the first and second posts are disposed at a distal end of the inner drive sleeve.

14. The surgical clip applier according to claim 12, wherein the inner drive sleeve defines a rectangular cross-sectional configuration including opposed narrow sides and opposed wide sides, and wherein the first and second posts are mounted along the narrow sides.

15. The surgical clip applier according to claim 11, wherein the first and second bearing rollers are disposed in parallel, spaced-apart relation relative to one another with the first and second spaced-apart arms disposed therebetween.

16. The surgical clip applier according to claim 11, wherein the first and second spaced-apart arms define inwardly-facing surfaces and outwardly-facing surfaces, the first and second bearing rollers configured to roll along the outwardly-facing surfaces of the first and second spaced-apart arms, respectively.

17. The surgical clip applier according to claim 16, wherein the outwardly-facing surfaces of the first and second spaced-apart arms define generally smooth, flat configurations.

18. The surgical clip applier according to claim 11, wherein the first and second spaced-apart arms are resiliently flexible from an at-rest position to a flexed position in response to movement of the bearing assembly from the proximal position to the distal position to thereby move the first and second jaws from the spaced-apart position to the approximated position.

19. The surgical clip applier according to claim 11, wherein the first and second spaced-apart arms are joined to one another via a proximal base, the proximal base fixed relative to the outer shaft.

20. The surgical clip applier according to claim 11, wherein the elongated assembly further includes a proximal hub disposed at a proximal end of the outer shaft, the proximal hub configured to releasably engage the elongated assembly with the handle assembly.

* * * * *